United States Patent [19]  [11] 4,110,463
Beard et al.  [45] Aug. 29, 1978

[54] IMIDAZOLE-2-CARBAMATES

[75] Inventors: Colin C. Beard, Saratoga; Marshall B. Wallach, Mountain View; Klaus Weinhardt, Redwood City, all of Calif.

[73] Assignee: Syntex (U.S.A.) Inc., Palo Alto, Calif.

[21] Appl. No.: 803,016

[22] Filed: Jun. 3, 1977

[51] Int. Cl.² .............. A61K 31/415; C07D 233/46; C07D 233/48
[52] U.S. Cl. .................... 424/273 R; 260/465 E; 260/570.5 P; 548/315
[58] Field of Search ............ 548/315; 424/273 R

[56] References Cited
U.S. PATENT DOCUMENTS
3,914,249   10/1975   Matier et al. .................... 548/315

OTHER PUBLICATIONS
Atkins et al., J. Chem. Soc. (London), Perkin Trans. I, 1973 (22), pp. 2644–2646.
Matier et al., J. Med. Chem., 1973, vol. 16, pp. 901–908.
Mengelberg Chem. Abst., 1959, vol. 53, columns 2210–2211.

Primary Examiner—Natalie Trousof
Attorney, Agent, or Firm—Tom M. Moran; William B. Walker

[57] ABSTRACT

Compounds represented by the formula

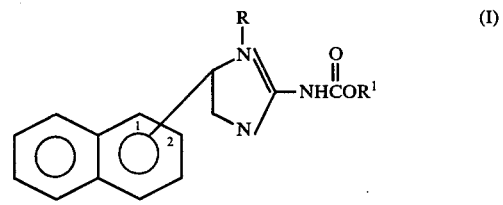

wherein R is hydrogen or alkyl of 1–4 carbons, $R^1$ is alkyl of 1–6 carbons and the naphthyl group is attached to the imidazole ring at the 1 or 2 positions of the naphthyl ring and the pharmaceutically acceptable salts thereof are useful as centrally acting skeletal muscle relaxants.

28 Claims, No Drawings

IMIDAZOLE-2-CARBAMATES

BACKGROUND OF THE INVENTION

1. Field of the Invention

This invention relates to imidazole-2-carbamates which are useful as centrally acting skeletal muscle relaxants. More specifically, the invention relates to 4,5-dihydro-2-alkoxycarbonylamino-4-(1-naphthyl)imidazole, 1-lower alkyl-4,5-dihydro-2-alkoxycarbonylamino-5-(1-naphthyl)imidazole, the corresponding 2-naphthyl isomers and the hydrogen anion salts thereof. The invention also relates to a pharmaceutically acceptable composition containing an effective amount of at least one of the compounds in combination with a suitable pharmaceutical excipient, the composition being useful for inducing skeletal muscle relaxation in mammals. The invention also relates to a process for making the compounds of the invention.

RELATED APPLICATIONS AND PRIOR ART

In copending U.S. Ser. No. 708,651, July 26, 1976 and U.S. Ser. No. 682,682, May 3, 1976, 1-alkyl-4,5-dihydro-2-alkoxycarbonylamino-5-(optionally substituted phenyl)imidazoles and 4,5-dihydro-2-alkoxycarbonylamino-4-(optionally substituted phenyl)imidazoles are disclosed. These compounds are primarily useful as anti-depressants although some exhibit centrally acting depressant and muscle relaxant activity. It is known that some 2-amino-4-aryl-2-imidazolines are useful as antihypertensive agents (Matier, et al, J. Med. Chem., 16, No 8, 901–908 (1973) and U.S. Pat. No. 3,914,249 to Matier, et al. It is also known that certain substituted imidazolocarbamides show anticonvulsant and cell respiratory inhibition activity. See Chaudhary, et al, J. Pharm. Sci., 65, No 7, 1010–1014 (1976). Trichloroethyl imidazolindin-2-ylenecarbamate is also known. See Atkins et al, J. Chem. Soc. (London) Perkins Trans. I, 1973 (22), pp 2644–6.

SUMMARY OF THE INVENTION

The first aspect of this invention is a compound chosen from those represented by the formula

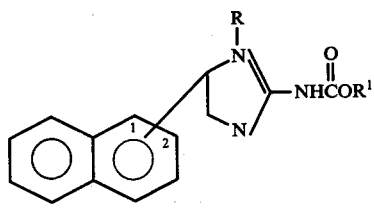

wherein R is hydrogen or alkyl of 1 through 4 carbon atoms (preferably hydrogen or alkyl of 1–2 carbon atoms), $R^1$ is alkyl of 1 through 6 carbon atoms (preferably 1–3 carbon atoms), the naphthyl group is attached through the 1 or 2 position of the naphthyl ring structure and the hydrogen-anion addition salts, preferably the pharmaceutically acceptable salts, thereof.

Another aspect of the invention is a method of producing a centrally induced muscle relaxant effect in mammals which comprises administering an effective amount of at least one compound chosen from those represented by the above formula.

Still another aspect of the invention is a composition useful for producing a muscle relaxant effect in mammals, which composition comprises an effective amount of at least one compound chosen from those represented by the formula I above and a pharmaceutically suitable excipient.

Still another aspect of the invention is a process for producing a compound of formula I above which comprises reacting a diamine, or suitable acid salt thereof, of the formula

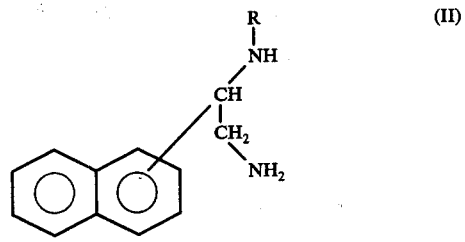

where R is previously defined with a suitable alkylating agent.

DETAILED DESCRIPTION AND PREFERRED EMBODIMENTS

Compounds of the Invention

Compounds of the invention are represented by the formula

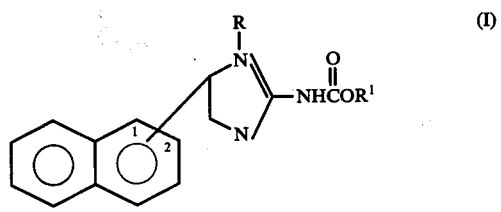

wherein R is hydrogen or alkyl of 1 to 4 carbon atoms, $R^1$ is alkyl of 1 through 6 carbon atoms, the naphthyl is attached at the 1 or 2 position of the naphthyl ring and the hydrogen-anion salts thereof, preferably the pharmaceutically acceptable salts thereof.

Preferably R is hydrogen or alkyl of 1 or 2 carbon atoms and $R^1$ is alkyl of 1–3 carbon atoms and the pharmaceutically acceptable salts thereof. Especially preferred of these compound are those of the 1-naphthyl series.

The term "alkyl" refers to an aliphatic, acyclic radical containing the number of carbon atoms indicated. An alkyl of 1 to 4 carbon atoms would include methyl, ethyl, isopropyl, n-propyl, n-butyl, isobutyl and t-butyl. The term "alkyl of 1–6 carbons" includes alkyls of 1–4 carbon atoms as well as n-amyl, isoamyl, t-pentyl, n-hexyl, isohexyl and the like.

The compounds of formula I have an asymmetric carbon atom (i.e. the imidazole ring carbon atom to which the naphthyl group is attached) and exist as optically acitve isomers. Thus, the above formula I is intended to represent the respective individual (+) and (−) optical isomers as well as mixtures thereof, and accordingly the individual isomers as well as the mixtures of isomers (e.g. racemic mixtures) are encompassed within the invention. Also, although the compounds of the invention wherein R is hydrogen will be named and described herein, for purposes of convenience, as 4,5-dihydro-2-alkoxycarbonylamino-4(1-naphthyl)imidazoles or 4,5-dihydro-2-alkoxycarbonylamino-4-(2-naphthyl) imidazoles, the compounds of the invention can exist in principle in any of the ring-tautomeric forms, below (A, B or C: 1-naphthyl shown), or the in protonated form as the hybrid structure D.

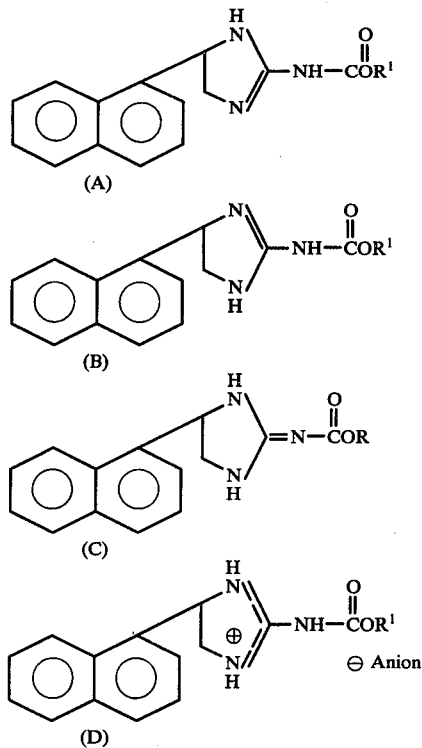

(A)

(B)

(C)

(D)

Hence, while the compounds of the invention are depicted as 4,5-dihydro-2-alkoxycarbonylamino-4-(1-naphthyl)imidazoles for purposes of brevity and convenience, it should be understood that all of the above forms of the compounds are encompassed within the structural and word formula designations and are encompassed within the invention. The same is true for 2-naphthyl compunds of formula I. Typical illustrations of 1-naphthyl compunds of formula I wherein R is hydrogen and $R^1$ is alkyl of 1–6 carbons are found in Example 1 while typical illustrations of corresponding 2-naphthyl compounds are found in Example 3.

The compunds of the invention wherein R is alkyl of 1–4 carbons and $R^1$ is alkyl of 1–6 carbons have an asymmetric carbon atom at the imidazole ring carbon to which the naphthyl group is attached. This carbon is designated in this series as the 5-carbon and thus these compounds also exist as optically active isomers. The above formula I is intended to represent the respective (+) and (−) optical isomers as well as mixtures thereof (racemic mixtures) and accordingly the individual isomers as well as the mixtures of the isomers are encompassed within the invention. Typical illustrations of 1-naphthyl compunds of formula I wherein R is alkyl of 1–4 carbons and $R^1$ is alkyl of 1–6 carbons are found in Example 2 while illustrations of 2-naphthyl compounds are found in Example 4.

Also included in the invention are the hydrogen-anion addition salts of the compound represented by formula I, that is, those salts of the parent compound made by reacting an organic or inorganic acid with a compound represented by formula I.

Preferably, the hydrogen-anion addition salts are pharmaceutically acceptable, i.e. those salts of the parent compound which do not significantly adversely effect the pharmaceutical properties (e.g. toxicity, effectiveness, etc.) of the parent compound and are conventionally used in the pharmaceutical art. Suitable pharmaceutically acceptable hydrogen-anion addition salts include (expressed with respect to the anion), for example, inorganic salts such as, for example, chloride, bromide, iodide, bisulfate, sulfate, phosphate, nitrate, and the like, or organic salts such as, for example, acetate, benzoate, lactate, propionate, butyrate, valerate, tartrate, maleate, fumarate, citrate, succinate, tosylate, ascorbic, palmitate, glyconate, adipate, and the like. Preferred pharmaceutically acceptable salts are the hydrochloride, bisulfate, hydrobromide, nitrate, maleate and citrate. The particularly preferred salts are the salts corresponding to the preferred group of compounds set forth above.

ADMINISTRATION AND FORMULATION

The compounds of this invention are useful for treating, palliating or preventing undesirable conditions, in mammals, involving the central nervous system, particularly as centrally acting skeletal muscle relaxants. Initial determination of the activity in mammals for a given compound can be obtained by applying routine experimental procedures such as those described by King and Unna in "The Action of Mephenesin and Other Interneuron Depressants on the Brain Stem", J. Pharmacol. Exp. Ther., 111, 293 (1954); or Barnett and Fiori in "Acute Tolerance to Diazepam in Cats and its Possible Relationship to Diazepam Metabolism". A more complete explanation of a modified procedure is given in Example 5, hereafter.

The compounds may be administered to mammals (especially humans) orally, rectally or parenterally (for example, by intraveneous, intraperitoneally or intramuscular injection). Where the compounds are administerally parenterally, they will, of course, be administered in liquid dosage forms, whereas when administered orally or rectally, they can be administered in either solid or liquid forms.

The amount administered is an effective amount i.e. that amount which is sufficient to produce the desired muscle relaxant effect. The exact amount required depends upon the particular subject and the intensity of the disorder being treated and can vary within wide limits such as, for example, between 0.01 and 300 mg. per kg. of body weight per day. Preferably, the amount will be about 0.1 to 100 mg/kg/day.

The pharmaceutical composition of this invention generally will include an effective amount of at least one compound of this invention in combination with a pharmaceutically suitable excipient, i.e. an inert vehicle. An effective amount is that amount which is effective to give the desired skeletal muscle relaxant effect in the mammal that is being treated using the recommended dosage. Thus the level of the drug in the formulation can vary from 0.1 percent weight (%w) to 99%w or more of the drug based on the total formulation and about 1%w to 99.9%w excipient. Preferably the drug is present at a level of 1%–95%w. The active ingredients of this invention can be formulated for oral, rectal or parental administration and may be liquid or solid for any of those means of administering. Preferably the pharmaceutical composition is formulated in unit dosage form to facilitate the simple administration of precise dosages. The pharmaceutically suitable excipient in the dosage form may comprise a carrier along with preservatives, emulsifying agents, wetting agents, buffering agents, and the like. Other compatible medicaments may also be included. Liquid dosage forms include, for example, solutions, suspensions, emulsions, syrups, elixers, etc. Liquid carriers include for example, water, saline solution, ethanol, and the like. Solid dosage forms include tablets, powders, capsules, pills, and the like. Suitable solid carriers which are useful in solid carriers as well as liquid carriers include for example, pharmaceutical grades of starch, lactose, sodium saccrahin, sodium bisulfate and the like. Conventional suppository carriers include polyethylene glycol, polysorbate, stearic acid, diglycol stearate, and the like.

PROCESS OF THE INVENTION

The compounds of this invention represented by formula I are prepared by reactively contacting a diamine of the formula

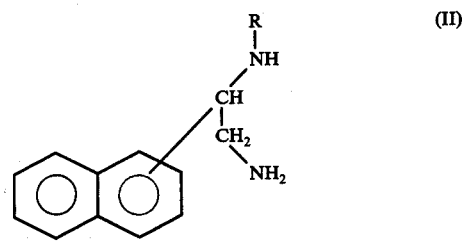

wherein the naphthyl is attached at the 1 or 2 positions and R is alkyl of 1–4 carbons with a suitable alkylating agent. Suitable alkylating agents include (i) a 1-mono- or 1,3-bis(alkoxycarbonyl)-S-methylisothiourea of the formula

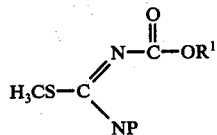

or mixtures thereof;

(ii) a 1-mono- or, 1,3-bis(alkoxycarbonyl)-S-alkoxycarbonyl isothiourea of the formula

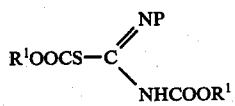

or mixtures thereof;

(iii) a mono- or bis(alkoxycarbony)cyanamide of the formula

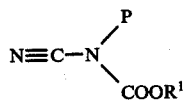

or mixtures thereof; or (iv) a compound represented by the formula

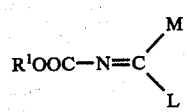

wherein $R^1$ is hereinbefore defined, P is hydrogen or —$COOR^1$, and M and L are independently chloro, alkoxy of 1–6 carbons or alkylthio of 1–6 carbons.

Generally, the reaction takes place in a suitable solvent at temperatures of about 15° C to reflux temperature for about 1 hour to 5 days. Suitable solvents include protic solvents such as oxygenated hydrocarbon solvents e.g. alcohols, like methanol, ethanol, isopropanol and the like, water; and mixtures thereof. Preferably an aqueous alcoholic solution is employed.

The preferred alkylating agent, 1-mono- or 1,3-bis(alkoxycarbonyl)-S-methyl isothiourea, is prepared by reacting thiourea with about equimolar amounts of methyl sulfate or methylchloroformate at elevated temperatures, e.g. about 20° to 100° C to form S-methyl isothiourea (or the $H_2SO_4$ or HCl salt thereof) which is then reacted with a molar excess of methyl chloroformate (more than 1 mole of the methylchloroformate per mole of the S-methyl isothiourea and preferably about 1.9–2.5 moles of the former per mole of the latter) in the presence of a suitable aqueous base, such as sodium hydroxide, potassium hydroxide and the like, at low temperatures of about 0° to 50° C for about 3 hours. The resulting alkylating agent is substantially insoluble in water and so may be filtered off and used in the process of this invention. Alternatively, the desired alkylating agent may be extracted with a suitable organic solvent such as a chlorinated hydrocarbon such as methylene chloride and the like, benzene, toluene, or other hydrocarbon solvents and isolated by evaporating the solvent. In still another alternative, the alkylating agent is utilized in situ to carry out the process of this invention.

The diamine represented by the formula II' wherein the naphthyl is attached at the 1-position is prepared according to the following reaction sequence

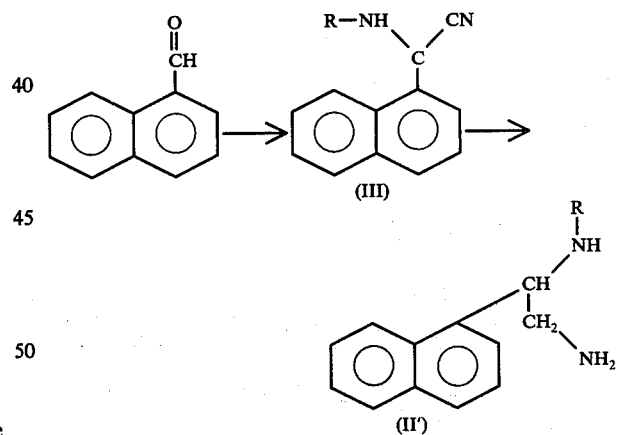

In the first step, 1-naphthaldehyde is reactively contacted with a suitable amine having the formula $RNH_2$, ammonia or a suitable salt thereof and an alkaline metal cyanide to form a cyano compound chosen from those represented by the formula III wherein R is alkyl of 1–4 carbon atoms. In the second step, the cyano compound represented by formula III is then reactively contacted with a suitable reducing agent to form a diamine chosen from those represented by Formula II' wherein R is as previously defined.

Suitable amines include methyl amine, ethyl amine, n-propyl amine, isopropyl amine, t-butyl amine and the like. Methyl amine, ethyl amine or ammonia and their hydrochloride salts are preferred. An alkaline metal cyanide includes lithium cyanide, potassium cyanide and, preferably, sodium cyanide. The reaction generally takes place in a suitable solvent such as water, methanol, ethanol or any other aliphatic alcohol, acetonitrile, diethylether, tetrahydrofuran, dioxane or a mixture of any of these. Particularly valuable as a solvent is aqueous dimethyl sulfoxide, that is dimethyl sulfoxide containing from 5 to 50%w water. The reaction readily takes place at temperatures from 5° to 50° C preferably about 20°-25° C with constant stirring. Reaction is generally completed in about 5 to 30 hours. The desired cyanide intermediate represented by formula III is readily isolated by first diluting with water and then extracting with benzene, drying, filtering and removing the solvent. Other suitable solvents for extraction are hexane, ether, chloroform or mixtures thereof.

In the second step, the cyanide compound represented by formula III is reacted with a suitable reducing agent such as lithium aluminum hydride, bis(methoxyethoxy) aluminum hdyride, diisobutylaluminum hydride, diborane, and the like. Lithium aluminum hydride has been found to be particularly valuable in this reaction. The reduction is carried out in a suitable solvent such as diethyl ether, tetrahydrofurane, benzene, hexane or mixtures of these, preferably diethyl ether. Generally the lithium aluminum hydride is first refluxed in diethyl ether for several hours before adding the cyanide compound. The reduction reaction takes place at temperatures of about −20° to 25° C. Preferably the cyanide is slowly added to the reducing agent, e.g. over a period of from one to five hours, depending, i.a., on the size of the batch being reacted.

PREPARATION

This sets forth a process for preparing 1,3-bis(methoxycarbonyl)-S-methylisothiourea according to the following reaction sequence.

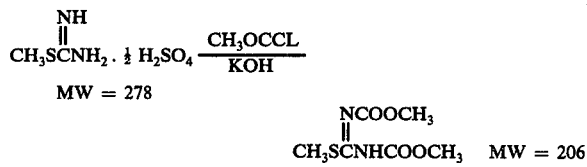

In a 4 liter erlenmeyer flask, 2-methyl-2-thiopseudourea, sulfate salt is stirred in 620 ml. $H_2O$ and cooled in an ice bath. Two hundred thirty-five milliliters (ml) of methylchloroformate is added at once and the resulting mixture kept between 10°-15° C. Thereafter, 310.5 grams of potassium hydroxide in 930 ml $H_2O$ is added over 2 hours keeping the pH basic. After the addition is completed, the product is extracted with methylene chloride, washed with brine, dried over sodium sulfate, filtered and the solvent removed on a rotary evaporator. The product is recrystalized from 350 ml methanol to yield a first crop of 126.7 g., m.p. 94°-98° C., 1,3-bis(methoxycarbonyl)-S-methylisothiourea.

The following representative examples are given to further enable one to prepare specific representative compounds of this invention, but are not intended to limit the scope of the claims appended hereto.

EXAMPLE 1

This example sets forth the process for making 4,5-dihydro-2-alkoxycarbonylamino-4-(1-naphthyl)-imidazoles.

A. This part sets forth a process for preparing 1-(1-naphthyl)-1,2-diaminoethane.

Elevan grams (g) of benzylamine in 90 milliliters (ml) of 1 N. hydrochloric acid and 16 g of 1-naphthaldehyde along with 50 ml of methanol are placed in a reaction vessel and cooled in an ice-water bath. Five g of sodium cyanide is added and stirred overnight. A white solid forms and the next day the mixture is diluted in the water, extracted with benzene and the extract washed with saturated sodium chloride solution then dried over potassium carbonate. The solvent is removed by rotary evaporator and the resulting substance is dried using an oil pump to give 28.5 g. of crystallized α-naphthyl-αbenzylaminoacetonitrile, melting point (m.p.) 62°-66° C.

Eight g of lithium aluminum hydride is refluxed in approximately 250 ml of ether for 4 hours and then is cooled to −10° C using an ice-methanol bath. Thereafter the α-naphthyl-α-benzylaminoacetonitrile prepared in the previous step is dissolved in about 200 ml of ether and the mixture is added over about 20 minutes keeping the reaction temperature at −10° C. The reaction mixture is stirred overnight while the bath is allowed to reach room temperature slowly. The next day the reaction mixture is cooled in an ice bath, then cautiously treated first with 8 ml of water, then with 8 ml of 15% sodium hydroxide and finally with 15 ml of water. The reaction is then stirred until the solid precipitate had turned from dark to nearly white. The precipitate is filtered and a mixture of 30 ml. of concentrated hydrochloric acid and 120 ml of isopropanol is added to the filtrate whereupon a white solid is formed. The solid is filtered, collected, washed with ether then dried to give 26 g of the dihydrochloride salt of 1-(1-naphthyl)-1-benzylamino-2-aminoethane, m.p. 241°-244°.

The resulting product is then placed in 500 ml. of ethanol and 80 ml of water along with 2 g of a 5% palladium on carbon catalyst and hydrogenated at atmospheric pressure with hydrogen (uptake 1.9/1) to give 15.5 g of crude 1-(1-naphthyl)-1,2-diaminoethane dihydrochloride having a melting point of about 330° C (with decomposition).

B. In this step a 1-naphthyl compound of formula I is prepared wherein R is hydrogen and $R^1$ is methyl.

The diamine, 1-(1-naphthyl)-1,2-diaminoethane dihydrochloride, as prepared in part A of this example (4.75 g) is dissolved in about 50 ml of water and 15 ml of saturated sodium bicarbonate solution is added followed by 3.5 g of 1,3-bis-(methoxycarbonyl)-S-methylisothiourea in 80 ml of chloroform, 5-10 ml of isopropanol and 330 mg of benzyltriethylammonium chloride. The reaction mixture is stirred for 4 days, then evaporated to dryness using a rotary evaporator. The solid residue is suspended in water, collected on a Buchner funnel, washed with water, suspended in fresh water and stirred for 2 hours. The solids are recollected, dried at room temperature in a vacuum desicator overnight to give 3.1 g of final product which is recrystalized from about 180 ml of toluene. The material is filtered, stored overnight, collected, and dried at 55° C overnight to give 2.1 g of 4,5-dihydro-2-(methoxycarbonylamino)-4-(1-naphthyl)imidazole having a m.p. of 208°-209° C.

To prepare the bisulfate salt, the product is dissolved in 25 ml of ethanol that contains 850 mg of sulfuric acid. This solution is added in portions to 300 ml of rapidly stirred ether to give 2.47 of the bisulfate salt C. Similarly, by following in principle the procedure of part B but substituting other 1,3-bis(alkoxycarbonyl)-S-methylisothioureas such as 1,3-bis(ethoxycarbonyl)-S-methylisothiourea; 1,3-bis(isopropoxycarbonyl)-S-methylisothiourea; 1,3-bis(n-propoxycarbonyl)-S-methylisothiourea; 1,3-bis(isobutoxycarbonyl)-S-methylisothiourea; 1,3-bis(n-pentyloxycarbonyl)-S-methylisothiourea; or 1,3-bis(n-hexyloxycarbonyl)-S-methylisothiourea for 1,3-bis(methoxycarbonyl)-S-methylisothiourea other corresponding compounds of Formula I are prepared, namely

- 4,5-dihydro-2-(ethoxycarbonylamino)-4-(1-naphthyl)imidazoles, m.p. 212°-213°;
- 4,5-dihydro-2-(isopropoxycarbonylamino)-4-(1-naphthyl)imidazole;
- 4,5-dihydro-2-(n-propoxycarbonylamino)-4-(1-naphthyl)imidazole;
- 4,5-dihydro-2-(isobutylcarbonylamino)-4-(1-naphthyl)imidazole;
- 4,5-dihydro-2-(n-pentylcarbonylamino)-4-(1-naphthyl)imidazole; and
- 4,5-dihydro-2-(n-hexylcarbonylamino)-4-(1-naphthyl)imidazole.

EXAMPLE 2

This example sets forth a process for making 1-alkyl-4,5-dihydro-2-alkoxycarbonylamino-5-(1-naphthyl)imidazoles.

A. This part sets forth a process for preparing 1-(1-naphthyl)-1-methylamino-2-aminoethane.

A mixture of 20 g of 1-naphthaldehyde, 75 ml of dimethylsulfoxide and 15 ml. of water is placed in an appropriate reaction flask and cooled momentarily with an ice bath. To this reaction mixture is then added 11 g of methylammonium hydrochloride followed by 8 g of sodium cyanide. The resulting mixture is stirred at room temperature under nitrogen for about 24 hours then partitioned between benzene and water. The aqueous layer is washed with additional benzene then the benzene layers combined, washed with water three times and once with a saturated brine solution. The resulting organic mixture is dried over sodium sulfate, filtered and the solvent evaporated off by a rotary evaporator to yield 24.3 g of an oily product containing α-(1-naphthyl)-α-methylaminoacetonitrile.

Nine and six tenths g of lithium aluminum hydride is added to 300 ml. of ether and refluxed for about 3 hours. The resulting mixture is cooled in an ice/methanol bath to about −15° C then 23 g of the oily product containing α-(1-naphthyl)-α-methylaminoacetonitrile in 150 ml of ether is slowly added to the mixture over an hour and a half while the temperature is kept between −10° and −15° C. The resulting mixture is stirred overnight while the ice bath is allowed to melt. In the morning the reaction mixture is cooled in an ice water bath then 10 ml of water followed by 10 ml of 15% of sodium hydroxide and 15 ml of water is slowly added to the reaction mixture to decompose any unreacted lithium aluminum hydride. The reaction mixture is then removed from the ice bath, stirred for an hour and filtered. The filtrate is swirled and 33 ml of 1 N HCl and 133 ml of isopropanol is slowly added. The resulting mixture is stirred, allowed to stand overnight and filtered. The precipitate is dried under vacuum to yield 23.6 g. of 1-(1-naphthyl)-1-methylamino-2-aminoethane, dihydrochloride.

B. This part sets forth a method for preparing the compound of this invention.

Six grams of 1-(1-naphthyl)-1-methylamino-2-aminoethane, dihydrochloride, prepared in Part A, are stirred into 25 ml of water. Thereafter 35 ml of saturated sodium bicarbonate are added and stirred for several minutes. Then 160 ml of isopropanol followed by 4.16 g of 1,3-bis(methoxycarbonyl)-S-methylisothiourea dissolved in 120 ml of chloroform are added to the mixture. The resulting mixture is stirred under nitrogen for 7 days. The organic solvents are removed in a rotary evaporator and 10% aqueous HCl is added until the pH of the mixture is just acidic. The resulting mixture is extracted with ether and the aqueous mixture is neutralized with saturated sodium bicarbonate, filtered, and pumped dry to give 5.3 g of crude 1-methyl-4,5-dihydro-2-(methoxycarbonylamino)-5-(1-naphthyl)-imidazole, m.p. 187°-190° C. One gram of the crude material is recrystallized from ethanol to give 0.77 g of more pure material, m.p. 194°-197° C.

The bisulfate salt of 1-methyl-4,5-dihydro-2-(methoxycarbonylamino)-S-(1-naphthyl)imidazole is prepared by treating 0.5 g of the recrystallized material with 8 ml of ethanol then adding 0.1 ml of concentrated sulfuric acid. The mixture is then added to 250 ml of ether while stirring. The resulting salt is filtered and dried to give 0.62 g of the bisulfate salt of 1-methyl-4,5-dihydro-2-(methoxycarbonylamino)-5-(1-naphthyl)-imidazole, m.p. 157°-158° C. This is recrystallized from ethanol to give .33 g. of more pure material, m.p. 163°-165°.

C. Similarly, by substituting other 1,3-bis(alkoxycarbonyl)-S-methylisothioureas such as 1,3-bis(ethoxycarbonyl)-S-methylisothiourea; 1,3-bis(isopropoxycarbonyl)-S-methylisothiourea; 1,3-bis(n-propoxycarbonyl)-S-methylisothiourea; 1,3-bis(t-butoxy carbonyl)-S-methylisothiourea; 1,3-bis(n-pentyloxycarbonyl)-S-methylisothiourea; or 1,3-bis(n-hexyloxycarbonyl)-S-methylisothiourea for 1,3-bis(methoxycarbonyl)-S-methylisothiourea the corresponding compounds of Formula I are prepared, namely

- 1-methyl-4,5-dihydro-2-(ethoxycarbonylamino)-5-(1-naphthyl)imidazole;
- 1-methyl-4,5-dihydro-2-(isoproxycarbonylamino)-5-(1-naphthyl)imidazole;
- 1-methyl-4,5-dihydro-2-(n-propoxycarbonylamino)-5-(1-naphthyl)imidazole;
- 1-methyl-4,5-dihydro-2-(t-butylcarbonylamino)-5-(1-naphthyl)imidazole;
- 1-methyl-4,5-dihydro-2-(n-pentylcarbonylamino)-5-(1-naphthyl)imidazole; and
- 1-methyl-4,5-dihydro-2-(n-hexylcarbonylamino)-5-(1-naphthyl)imidazole.

D. By following in principle the procedure of Part A-C but substituting other alkylammonium hydrochlorides having 2-4 carbons in the alkyl group such as ethylammonium hydrochloride, isopropylammonium hydrochloride, n-propylammonium hydrochloride, n-butylammonium hydrochloride, or t-butylammonium hydrochloride for methylammonium hydrochloride, other corresponding compounds of formula I are prepared, namely

- 1-ethyl-4,5-dihydro-2-(methoxycarbonylamino)-5-(1-naphthyl)imidazole;
- 1-isopropyl-4,5-dihydro-2-(methoxycarbonylamino)-5-(1-naphthyl)-imidazole;

1-n-propyl-4,5-dihydro-2-(methoxycarbonylamino)-5-(1-naphthyl)-imidazole;

1-n-butyl-4,5-dihydro-2-(methoxycarbonylamino)-5-(1-naphthyl)-imidazole; and 1-t-butyl-4,5-dihydro-2-(methoxycarbonylamino)-5-(1-naphthyl)-imidazole.

E. Similarly, by substituting other 1,3-bis(alkoxycarbonyl) S-methyl-isothioureas such as those set forth in Part C of this example in combination with the alkylammonium chlorides in Part D, other 1-alkyl-4,5-dihydro-2-(alkoxycarbonylamino)-5-(1-naphthyl)-imidazoles are prepared such as 1-ethyl-4,5-dihydro-2(-ethoxycarbonylamino)-5-(1-naphthyl)imidazole;

1-ethyl-4,5-dihydro-2(-isoproxycarbonylamino)-5-(1-naphthyl)imidazole;

1-ethyl-4,5-dihydro-2(-n-butoxycarbonylamino)-5-(1-naphthyl)imidazole;

and the like.

EXAMPLE 3

This example sets forth a process for preparing 4,5-dihydro-2-(alkoxycarbonylamino)-4-(2-naphthyl)imidazoles.

A. This part presents a process for preparing 1-(2-napthyl)-1,2-diaminoethane, dihydrochloride. One hundred sixty-nine ml of 10% hydrochloric acid is placed in a 3-neck reaction flask and cooled in an ice bath. To the cooled, stirred acid is added, in order, 21 ml benzylamine, 30 g 2-naphthaldehyde, 94 ml methanol and 9.4 g sodium cyanide. The mixture is removed from the ice bath and stirred under nitrogen for about 18 hours. The mixture is diluted with water, and extracted with benzene. The benzene solution is washed with a brine solution, dried over sodium sulfate, filtered and the solvent removed by rotary evaporator to give 34 g of a product containing α-(2-naphthyl)-α-benzylaminoacetonitrile. The crude product is added to 350 ml of a mixture of ether in tetrahydrofuran (3:1).

Five hudnred ml of ether is added to a 1000 ml 3-neck reaction flask and stirred under nitrogen for several minutes after which time 11 g of lithium aluminum hydride is added and the mixture refluxed for 2½ hours then cooled in an ice/methanol bath. A mixture of the 34 g of the product containing the acetonitrile in 350 ml ether/tetrahydrofuran is added over a period of about 55 minutes while the reactants are stirred and cooled using the methanol/ice bath. The resulting mixture is stirred for about 17 hours while allowing it to gradually warm to room temperature. To decompose any remaining lithium aluminum hydride, 11 ml water, 11 ml 15% aqueous sodium hydroxide, and 16.5 water are slowly and consecutively added to the reaction mixture. The resulting mixture is filtered and the filtrate is slowly mixed with 57 ml hydrochloric acid in 225 ml of isopropanol while stirring. The resulting precipitate is filtered and dried to give 21.03 g of crude 1-(2-naphthyl)-1-benzylamino-2-aminoethane. Eleven g of this product is recrystallized from ethanol after filtering in a hot ethanol solution to give 9.37 g of more pure 1-(2-naphthyl)-1-benzylamino-2-aminoethane m.p. 245°–251° C.

The product is hydrogenated to remove the benzyl group by placing 253.5 ml ethanol, 12.7 ml water, 9.3 g 1-(2-naphthyl)-1-benzylamino-2-aminoethane (m.p. 245°–251° C) and 3.38 g 10% palladium on carbon catalyst in a suitable hydrogenation vessel and 625 ml hydrogen is added thereto over a 75 minute period. The reaction mixture is filtered through diatomaceous earth and the solvent removed on a rotary evaporator to give 8.2 g of a product containing 1-(2-naphthyl)-1,2-diaminoethane, dihydrochloride. The crude product is recrystallized from ethanol to give 2.6 g of a product which decomposes at about 270° C.

B. This part sets forth a process for preparing 4,5-dihydro-2-(methoxycarbonylamino)-4-(2-naphthyl)imidazole.

One g of the recrystallized product from part A and 7.5 ml saturated sodium bicarbonate are added to a reaction flask and stirred under nitrogen for several minutes. Thirty-two ml isopropanol are added followed by 1.2 g of 1,3-bis(methoxycarbonyl)-S-methylisothiourea in 24 ml chloroform and the resulting mixture is stirred at room temperature (about 20° C) for about 5 days. Thereafter, the solvent is removed by rotary evaporator, the residue dissolved in 10% aqueous hydrochloric acid, washed with ether, and saturated sodium bicarbonate added to the aqueous layer. The resulting precipitate is stirred, filtered and dried to give 0.70 g of a product containing 4,5-dihydro-2-(methoxycarbonylamino)-4-(2-naphthyl)-imidazole m.p. 140°–180° C. The crude product is further purified using column chromatography by placing 500 mg on a column containing 75 g silica gel and eluting with 1700 ml 5% methanol in benzene made basic with ammonium hydroxide followed by 1700 ml 10% methanol in benzene made basic with ammonium hydroxide. The eluant is collected in 20 ml fractions. Fractions 15–28 are combined and the solvent is removed by rotary evaporator. This gives 94.1 mg of a white solid m.p. 215°–218° C. This white solid is recrystallized from methanol to give 45.5 mg of 4,5-dihydro-2-(methoxycarbonylamino)-4-(2-naphthyl)imidazole white solid, m.p. 227°–228° C.

C. Similarly, by following in principle the procedure of part B but substituting other 1,3-bis(alkoxycarbonyl)-S-methylisothioureas such as 1,3-bis(ethoxycarbonyl)-S-methylisothiourea; 1,3-bis(isopropoxycarbonyl)-S-methylisothiourea; 1,3-bis(n-propoxycarbonyl)-S-methylisothiourea; 1,3-bis(t-butoxycarbonyl)-S-methylisothiourea; 1,3-bis(n-pentyloxycarbonyl)-S-methylisothiourea; or 1,3-bis(n-hexyloxycarbonyl)-S-methylisothiourea for 1,3-bis(methoxycarbonyl)-S-methylisothiourea other corresponding compounds of Formula I are prepared, namely 4,5-dihydro-2-(ethoxycarbonylamino)-4-(2-naphthyl)imidazole;

4,5-dihydro-2-(isoproxycarbonylamino)-4-(2-naphthyl)imidazole;

4,5-dihydro-2-(n-propoxycarbonylamino)-4-(2-naphthyl)imidazole;

4,5-dihydro-2-(t-butoxycarbonylamino)-4-(2-naphthyl)imidazole;

4,5-dihydro-2-(n-pentyloxycarbonylamino)-4-(2-naphthyl)imidazole; and 4,5-dihydro-2-(n-hexyloxycarbonylamino)-4-(2-naphthyl)imidazole.

EXAMPLE 4

This example sets forth a process for making 1-alkyl-4,5-dihydro-2-alkoxycarbonylamino-5-(2-naphthyl)imidazoles.

A. By following in principle the procedure of part A of Example 2, 1-(2-naphthyl)-1-methylamino-2-aminoethane is prepared.

B. By following in principle the procedure of part B of Example 2, 1-methyl-4,5-dihydro-2-(methoxycarbonylamino)-5-(2-naphthyl)imidazole, or its bisulfate, is prepared.

C. Similarly, by substituting other 1,3-bis(alkoxycarbonyl)-s-methylisothioureas such as 1,3-bis(ethoxycarbonyl)-S-methylisothiourea; 1,3-bis(isopropoxycarbonyl)-S-methylisothiourea; 1,3-bis(n-propoxycarbonyl)-S-methylisothiourea; 1,3-bis(isobutoxycarbonyl)-S-methylisothiourea; 1,3-bis(n-pentyloxycarbonyl)-S-methylisothiourea; or 1,3-bis(n-hexyloxycarbonyl)-S-methylisothiourea for 1,3-bis(methoxycarbonyl)-S-methylisothiourea the corresponding compounds of Formula I are obtained, namely 1-methyl-4,5-dihydro-2-(ethoxycarbonylamino)-5-(2-naphthyl)imidazole;

1-methyl-4,5-dihydro-2-(isoproxycarbonylamino)-5-(2-naphthyl)-imidazole;

1-methyl-4,5-dihydro-2-(n-propoxycarbonylamino)-5-(2-naphthyl)-imidazole;

1-methyl-4,5-dihydro-2-(t-butoxycarbonylamino)-5-(2-naphthyl)-imidazole;

1-methyl-4,5-dihydro-2-(n-pentyloxycarbonylamino)5-(2-naphthyl)-imidazole; and 1-methyl-4,5-dihydro-2-(n-hexyloxycarbonylamino)-5-(2-naphthyl)-imidazole.

D. By following in principle the procedure of Part A but substituting other alkylammonium hydrochlorides having 2-4 carbons in the alkyl group such as ethylammonium hydrochloride, isopropyl ammonium hydrochloride, n-propylammonium hydrochloride, n-butylammonium hydrochloride, or t-butylammonium hydrochloride for methylammonium hydrochloride, other corresponding compounds of formula I are prepared, namely 1-ethyl-4,5-dihydro-2-(methoxycarbonylamino)-5-(2-naphthyl)imidazole;

1-isopropyl-4,5-dihydro-2-(methoxycarbonylamino)-5-(2-naphthyl)imidazole;

1-n-propyl-4,5-dihydro-2-(methoxycarbonylamino)-5-(2-naphthyl)imidazole;

1-n-butyl-4,5-dihydro-2-(methoxycarbonylamino)-5-(2-naphthyl)imidazole; and 1-t-butyl-4,5-dihydro-2-(methoxycarbonylamino)-5-(2-haphthyl)imidazole.

E. Similarly, by substituting other 1,3-bis(alkoxycarbonyl)-S-methyl-isothioureas such as those set forth in Part C of this example in combination with the alkylammonium hydrochlorides in Part D, other 1-alkyl-4,5-dihydro-2-(alkoxycarbonylamino)-5-(2-naphthyl)-imidazoles may be prepared such as 1-ethyl-4,5-dihydro-2(-ethoxycarbonylamino)-5-(2-naphthyl)imidazole;

1-ethyl-4,5-dihydro-2(-isopropoxycarbonylamino)-5-(2-naphthyl)imidazole;

1-ethyl-4,5-dihydro-2(-n-butoxycarbonylamino)-5-(2-naphthyl)imidazole; and the like.

EXAMPLE 5

CENTRALLY ACTING SKELETAL MUSCLE RELAXANT ASSAY—CAT LINGUOMANDIBULAR RELFEX PREPARATION

This assay is used to assess the centrally acting skeletal muscle relaxant properties of compounds of this invention. Mongrel cats weighing 2–5 kg are anesthetized with phenobarbital sodium, 180 mg/kg, i.p. The anesthetized cat is placed in a sterotaxic headholder, shaved, and the femoral artery and vein are cannulated. The cannula from the femoral artery is connected to a Statham Model P-23 AC Transducer in order to monitor blood pressure. The femoral vein is utilized for the administration of drugs.

The cat is placed in a prone position and two electrodes, consisting of wound clips soldered to wires, are attached bilaterally to the base of the tongue. These leads are then connected to a Grass S8 stimulator. A Grass FT-03 Transducer is placed beneath the jaw. A round platform approximately 4 cm in diameter rests against the lower jaw and conducts the movement of the jaw to the transducer. Signals from the transducers are recorded on a Beckman Polygraph.

The stimulator is set to deliver single pulses of 2.5 millisecond duration. A determination is made of the voltage necessary to produce a maximal response. The stimulator is then set a 1 volt higher than this maximal voltage. Upon determination of the supramaximal theshold, the tongue is stimulated every 10 seconds. Once the response is determined to be stable, drug solution is administered i.v. in logarithmically spaced doses. Each cat receives several doses of only one test compound. The doses are always administered in an ascending order. Recovery from an individual dose is allowed prior to the next dose administration.

The percent reduction of the jaw opening reflex is utilized for determining the activity of the drug, the greater the percent reduction the more active the compound.

We claim as our invention:

1. A compound chosen from those represented by the formula

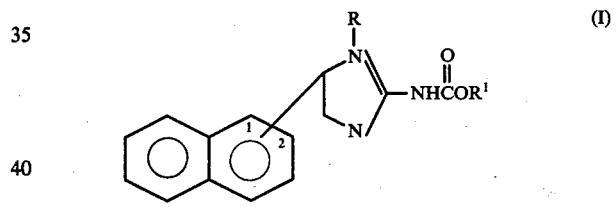

wherein R is hydrogen or alkyl of 1 through 4 carbon atoms $R^1$ is alkyl of 1 through 6 carbon atoms, and the naphthyl group is attached at the 1- or 2- position of the naphthyl structure and the hydrogen anion addition salts thereof.

2. The compound of claim 1 wherein R is hydrogen or alkyl of 1 through 2 carbon atoms and $R^1$ is alkyl of 1 through 3 carbon atoms.

3. The compound of claim 2 wherein the naphthyl group is attached at the 1-position of the naphthyl structure.

4. The compound of claim 3 wherein R is hydrogen and $R^1$ is methyl; 4,5-dihydro-2-methoxycarbonylamino-4-(1-naphthyl)-imidazole and the pharmaceutically acceptable salts thereof.

5. The compound of claim 3 wherein R is hydrogen and $R^1$ is ethyl; 4,5-dihydro-2-ethoxycarbonylamino-4-(1-naphthyl)-imidazole and the pharmaceutically acceptable salts thereof.

6. The compound of claim 3 wherein R is methyl and $R^1$ is methyl; 1-methyl-4,5-dihydro-2-methoxycarbonylamino-5-(1-naphthyl)-imidazole and the pharmaceutically acceptable salts thereof.

7. The compound of claim 3 wherein R is methyl and $R^1$ is ethyl; 1-methyl-4,5-dihydro-2-ethoxycarbonylamino-5-(1-naphthyl)-imidazole and the pharmaceutically acceptable salts thereof.

8. The compound of claim 3 wherein R is methyl and $R^1$ is isopropyl; 1-methyl-4,5-dihydro-2-isopropoxycarbonylamino-5-(1-naphthyl)-imidazole and the pharmaceutically acceptable salts thereof.

9. The compound of claim 3 wherein R is ethyl and $R^1$ is methyl; 1-ethyl-4,5-dihydro-2-methoxycarbonylamino-5-(1-naphthyl)-imidazole and the pharmaceutically acceptable salts thereof.

10. The compound of claim 3 wherein R and $R^1$ are both ethyl; 1-ethyl-4,5-dihydro-2-ethoxycarbonylamino-5-(1-naphthyl)-imidazole and the pharmaceutically acceptable salts thereof.

11. The compound of claim 3 wherein R is ethyl and $R^1$ is isopropyl; 1-ethyl-4,5-dihydro-2-isopropoxycarbonylamino-5-(1-napthyl)-imidazole and the pharmaceutically acceptable salts thereof.

12. The compound of claim 1 wherein the naphthyl group is attached at the 2-position of the naphthyl structure.

13. The compound of claim 12 wherein R is hydrogen and $R^1$ is methyl; 4,5-dihydro-2-methoxycarbonylamino-4-(2-naphthyl)imidazole 14. A method of producing a muscle relaxant effect in mammals which comprises administering an effective amount of at least one compound chosen from those represented by the formula

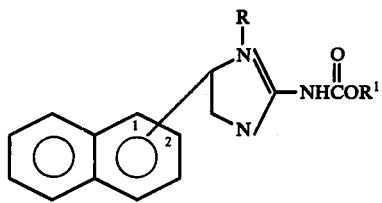

wherein R is hydrogen or alkyl of 1 through 4 carbon atoms, $R^1$ is alkyl of 1 through 6 carbon atoms, and the naphthyl group is attached at the 1- or 2- position of the naphthyl structure and the pharmaceutically acceptable salts thereof.

15. The method of claim 14 wherein said compound is chosen from those represented by formula (I) wherein R is hydrogen or alkyl of 1 or 2 carbon atoms and $R^1$ is alkyl of 1 through 3 carbon atoms.

16. The method of claim 14 wherein said compound is administered to said mammal at the rate of 0.01 to 300 milligrams per kilogram of body weight.

17. The method of claim 16 wherein said mammal is a human and said compound is administered at a rate of 0.1 to 100 milligrams per kilogram body weight.

18. The method of claim 17 wherein said compound is administered orally in a suitable pharmaceutical dosage form.

19. A composition useful for producing a muscle-relaxant effect in mammals, which composition comprises (a) an effective amount of at least one compound chosen from those represented by the formula

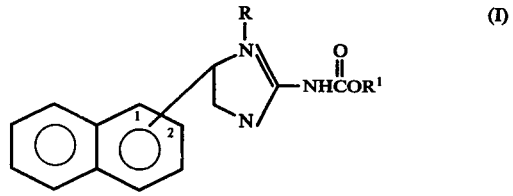

wherein R is hydrogen or alkyl of 1 through 4 carbon atoms, $R^1$ is alkyl of 1 through 6 carbon atoms, and the naphthyl group is attached at the 1- or 2- position of the naphthyl structure and the pharmaceutically acceptable salts thereof and (b) pharmaceutically suitable excipients.

20. The composition of claim 19 wherein R is hydrogen or alkyl of 1 or 2 carbon atoms and $R^1$ is alkyl of 1 through 3 carbon atoms.

21. The composition of claim 20 wherein said compound is 4,5-dihydro-2-methoxycarbonylamino-4-(1-naphthyl)-imidazole or the pharmaceutically acceptable salts thereof.

22. The composition of claim 21 wherein said compound is 4,5-dihydro-2-ethoxycarbonylamino-4-(1-naphthyl)-imidazole or the pharmaceutically acceptable salts thereof.

23. The composition of claim 20 wherein said compound is 1-methyl-4,5-dihydro-2-methoxycarbonylamino-5-(1-naphthyl)-imidazole or the pharmaceutically acceptable salts thereof.

24. The composition of claim 20 wherein said compound is 1-methyl-4,5-dihydro-2-ethoxycarbonylamino-5-(1-naphthyl)-imidazole or the pharmaceutically acceptable salts thereof.

25. The composition of claim 20 wherein said compound is 1-methyl-4,5-dihydro-2-isopropoxycarbonylamino-5-(1-naphthyl)-imidazole or the pharmaceutically acceptable salts thereof.

26. The composition of claim 20 wherein said compound is 1-ethyl-4,5-dihydro-2-methoxycarbonylamino-5-(1-naphthyl)-imidazole or the pharmaceutically acceptable salts thereof.

27. The composition of claim 20 wherein said compound is 1-ethyl-4,5-dihydro-2-ethoxycarbonylamino-5-(1-naphthyl)-imidazole or the pharmaceutically acceptable salts thereof.

28. The composition of claim 20 wherein said compound is 1-ethyl-4,5-dihydro-2-isopropoxycarbonylamino-5-(1-naphthyl)-imidazole or the pharmaceutically acceptable salts thereof.

* * * * *